United States Patent [19]

Harth et al.

[11] 4,193,987
[45] Mar. 18, 1980

[54] NON-CORROSIVE TOOTHPASTE

[75] Inventors: Helmut Harth, Mainz; Dieter Becker, Darmstadt-Wixhausen, both of Fed. Rep. of Germany

[73] Assignee: Blendax-Werke R. Schneider GmbH & Co., Mainz, Fed. Rep. of Germany

[21] Appl. No.: 971,227

[22] Filed: Dec. 20, 1978

[30] Foreign Application Priority Data

Dec. 22, 1977 [DE] Fed. Rep. of Germany ....... 2757280

[51] Int. Cl.$^2$ .............................................. A61K 7/16
[52] U.S. Cl. ...................................... 424/49; 424/357
[58] Field of Search .................................. 424/49–58, 424/357

[56] References Cited

U.S. PATENT DOCUMENTS 4,132,771   1/1979   Schreiber et al. .................... 424/52

*Primary Examiner*—Shep K. Rose
*Attorney, Agent, or Firm*—Connolly and Hutz

[57] ABSTRACT

The corrosive effect of toothpaste on aluminum is prevented by incorporating in the toothpaste about 0.05% to about 5% by weight of a synthetic alkali metal aluminum silicate zeolite. Toothpaste containing a zeolite of the empirical formula $Na_{12}(AlO_2)_{12}\cdot(SiO_2)_{12}\cdot 27H_2O$ is particularly useful.

4 Claims, No Drawings

NON-CORROSIVE TOOTHPASTE

The present invention relates to a toothpaste which has no corrosive effect on bare aluminum surfaces and which contains synthetic zeolite of the alkali aluminum silicate type as the corrosion-preventing agent.

Most of the polishing agents proposed for use in toothpastes have the drawback that they exert a corrosive effect on bare, i.e. unlacquered, aluminum surfaces. Thus the aluminum toothpaste tubes being used must be provided with an inner protective lacquer, which raises the cost for the packaging material and consequently also for the finished toothpaste. Furthermore, with possible damages to the inner protective lacquer film, it can lead to "knobbing" of the toothpaste tubes and consequently to reclamations.

It has now been found that a non-corrosive toothpaste can be prepared if an alkali aluminum silicate of the zeolite type in concentrations of 0.05 to 5% by weight is added to this toothpaste.

These zeolite compounds have been known for a long time. They are used per se as molecular filters, for water softening and recently also in washing preparations as substitutes for phosphates otherwise used as inorganic builders. The zeolites are water-containing framework silicates which can be expressed by the general formula $x(M.AlO_2).ySiO_2.zH_2O$, wherein M is alkali or ammonium, x is a number between 1 and 64, y is a number dependent on x with the determination of y being one-fold to six-fold of x, and z is a number between 0 and 256.

The synthetic zeolites used in toothpastes as polishing agents according to the invention may be prepared in a simple known manner from aluminum hydroxide and alkali silicates such as water glass. A product particularly suitable within the scope of the present invention is zeolite A with the empirical formula $Na_{12}(AlO_2)_{12}.(SiO_2)_{12}.27H_2O$. Such a product is sold by the company Degussa under the trade name "Sasil" and has an average particle size of about 4 microns, an apparent density of about 400 g/l and a loss on ignition of about 20% (1 h at 800° C.). The zeolites being used are insoluble in water. Their average standard particle size is preferably between about 1 and about 30 microns. A summary of the preparation and the properties of the alkali aluminum silicates being used according to the invention is given by F. Schwochow and L. Puppe, "Angewandte Chemie" (Applied Chemistry) 87 (1975), pp. 659–667.

German published application No. 2 146 224 discloses transparent and translucent toothpastes which contain a synthetic amorphous complex alkali or alkaline earth aluminum silicate as the cleaning substance which has a refractive index of about 1.44 to 1.47. The alkali aluminum silicates described there differ essentially from the products used in this invention, however, since they are not synthetic zeolites. Furthermore, the subject matter of the German published application is completely different with respect to the object of the present invention which is directed to preparation of anticorrosive toothpastes. The novel toothpastes of this invention must not be transparent or translucent and, indeed, the refractive index of the zeolites used according to this invention lies outside the range required for transparent toothpastes.

Corrosive polishing agents which may be used jointly with the corrosion-stabilizing zeolite in the novel toothpastes are, for example, the various calcium phosphates such as dicalciumorthophosphate in its anhydrous or hydrated form, calcium pyrophosphate and tricalciumphosphate, calcium or magnesium carbonate, aluminum hydroxide or insoluble alkali metaphosphate. The proportion of the polishing agent is customarily between 15 and 60 and particularly between 20 and 40% of the mass.

Numerous suggestions have already been made for incorporating corrosion-preventing additives in toothpastes. Representative of the prior art are German published applications No. 1 953 943, which suggests the addition of monofluorophosphates, No. 1 953 944, which relates to the application of orthophosphates, No. 2 509 399, which discloses silica brine whose particles are negatively charged, and No. 2 600 709, which uses surface-active anionic phosphate esters for this purpose. The corrosion stabilizers described here, however, all have the drawback that they would be suitable only for toothpastes containing aluminum hydroxide as the polishing agent. The corrosion stabilizers of the invention, however, are suitable for stabilizing toothpastes containing all types of polishing agents.

The application of sodium silicates as anticorrosive additives in toothpastes is known per se.

However, this relates to simple alkali silicates such as sodium silicate ($Na_2SiO_3$) and not to the alkali aluminum silicates used according to the invention which have the general formula $x(M.AlO_2).ySiO_2.zH_2O$ and are of the zeolite type.

These known corrosion-preventing agents have the great disadvantage that they are effective only at pH values of 8.5 and above. Thus, the known corrosion-preventive agents are paractical only in alkaline toothpastes which contain calcium carbonate as the polishing agent. The alkali silicates at pH values of less than 8.5, which most toothpastes exhibit, the alkali silicates have no corrosion-preventing properties for aluminum customarily employed in toothpaste tubes.

The corrosion-preventing agents of this invention are not dependent on pH for their corrosion-preventive properties. They may be used in toothpastes with any desired polishing agent. This is of particular importance especially in view of the known fluoride-containing caries-prophylactic toothpastes which have weakly acid pH values. This effect of the complex aluminum silicates of a certain structure of the zeolite type used according to the invention was particularly unexpected because those skilled in the art with knowledge of the behavior of the simple alkali silicates would have expected that the zeolites also would be effective only in the alkaline medium.

British Pat. No. 1 476 063 mentions the use of sodium silicate as an anticorrosive agent. The pastes described there have an alkaline pH value because of the calcium carbonate polishing agent used. The "aluminosilicates" also described in this reference differ basically from the zeolites used according to this invention by the proportion of aluminum to silicon, which is far outside the proportions found in the zeolites used according to this invention (see particularly page 1, lines 38–42 of the British patent).

British Pat. No. 332 142 relates to tooth powder containing a zeolite as the calcium ion complex former. There is no disclosure or recognition in this reference of a corrosion-preventing property of the zeolite in toothpaste tubes. The single example of British Pat. No. 332 142 describes use of about 40% of the mass zeolite in a tooth powder and lies far outside the quantity limits defined by our invention for the introduction of zeolite as a corrosion-preventing agent. The object and even more so the solution of the problem by the current invention cannot be found in British Pat. No. 332 142.

The same is true with respect to German Pat. No. 378 010, which also describes the use of zeolite as the alkaline earth ion complex former in tooth-cleaning compositions.

The novel toothpastes of this invention contain the customary fillers and synthesizing substances. Used as moisture-holding agents are glycerine, polyglycols with low molar weight or sugar alcohols such as sorbite, mannite and xylite.

Furthermore, toothpastes contain thickening agents. Best suited as such are the alkali salts of carboxymethyl cellulose, particularly sodium carboxymethyl cellulose; hydroxyalkyl cellulose, particularly hydroxyethyl cellulose; plant gums, such as tragacanth; gum arabic; caraya gum; and Irish moss; synthetic polyelectrolyte, such as sodium, potassium or ammonium salt of polyacrylic acid; and also inorganic thickening agents, e.g. colloidal magnesium aluminum silicate.

The proportion of the thickening agent is about 0.25 to 5% by weight of the toothpaste.

Toothpastes also contain surface-active substances. Suitable as such in particular are water-soluble salts of higher alkyl sulfates, e.g. sodium lauryl sulfate; aliphatic acylamides of saturated monoaminocarboxylic acids; preferably sodium-N-lauroylsarcosinate, taurine fatty acidamides, e.g. sodium-N-alkyl-N-myristoyl tauride; salts of sulfonated monoglycerides of higher fatty acids, e.g. sodium monoglyceride sulfonate; fatty acid esters of isethionic acid and the salts thereof; nonionic surface-active agents such as alkylene oxide condensates with fatty alcohols and mono or polyvalent amines; sugar esters, e.g. saccharose monolaurate, sorbitol polyoxyethylene stearate; long-chain amine oxides, e.g. dimethyllaurylamino oxide; ampholytical surface-active agents, e.g. betains or long-chain alkylaminocarboxylic acids and cation-active surface-active agents, e.g. quaternary ammonium compounds such as cetyl trimethyl ammonium bromide.

The proportion of surface-active compounds in the novel tooth-cleaning composition is 0 to about 5% by weight of the total composition.

Tooth-cleaning compositions normally contain aromatic and flavoring substances, preserving agents, and so forth. Those agents are known and are described in numerous publications.

It is a preferred embodiment of the invention to use fluorine compounds in the novel tooth-cleaning compositions, preferably in such a quantity that the concentration of pure fluorine in the agent is 0.01 to 1% by weight, and preferably 0.1 to 0.5% by weight, of the tooth-cleaning composition.

Suitable fluorine compounds in particular are the various salts of monofluorophosphoric acid, particularly sodium, potassium, lithium, calcium and aluminum mono and difluorophosphate, as well as the various fluorides containing fluorine in ion-bound form, particularly alkalifluorides such as sodium, lithium, potassium and ammonium fluoride, stannous fluoride, manganese fluoride, zirconium fluoride and aluminum fluoride as well as compositions or addition products of these fluorides among themselves or with other fluorine compounds, e.g. potassium or sodium manganese fluoride.

Other fluorides usable within the scope of the present invention are, for example, zinc fluoride, germanium fluoride, palladium fluoride, titanium fluoride, alkalifluorozirconates, e.g. sodium or potassium fluorozirconate, stannous fluorozirconate, fluoroborate or fluorosulfate, e.g. sodium or potassium fluoro sulfate.

Organic fluorine compounds can also be used successfully, particularly the known addition products of long-chain amines or amino acids and hydrogen fluoride, monoethanolaminohydrofluoride or methyltriethyl ammonium fluoride.

The tooth-cleaning compositions of the invention may contain further substances known for use in such agents, e.g. enzymes such as proteases and carbohydrases, such as amylase, dextranase, levanase or $\alpha$-1,3-glucane-3-glucanohydrolase, tartar-removing substances such as the phosphonic acids suggested for this purpose, e.g. hydroxyethane-1,1-diphosphonic acid, or the bisbiguanides 1,6-di-4'-(chlorophenyldiguanido) hexane, 1,6-di-4'-(fluorophenyldiguanido) hexane and 1,6-di-(2-ethylhexyldiguanido) hexane or the preferably water-soluble salts thereof, known under the names "chlorhexidin", "fluorhexidin" or "alexidin".

A detailed summary of the preparation of the tooth-cleaning compositions and the substances used therein is given in the manual by M. S. Balsam and E. Sagarin, "Cosmetics-Science and Technology" 2nd Ed., Vol. 1, pp 423–532 (1972).

Below are examples of the tooth-cleaning compositions prepared in accordance with this invention:

EXAMPLE 1

| | |
|---|---|
| carboxymethyl cellulose | 1.20% by weight |
| p-hydroxybenzoic acid propyl ester, sodium salt | 0.10% by weight |
| formalin | 0.10% by weight |
| sorbitol, 70% | 12.00% by weight |
| sodiummonofluorophosphate | 0.75% by weight |
| aroma | 1.00% by weight |
| saccharinate sodium | 0.08% by weight |
| sodium lauryl sulfate | 1.80% by weight |
| calcium carbonate | 35.00% by weight |
| sodium aluminum silicate (zeolite A, $Na_{12}(AlO_2)_{12}(SiO_2)_{12} \cdot 27H_2O$) | 1.00% by weight |
| allantoin | 0.20% by weight |
| pyrogenic silicic acid | 2.00% by weight |
| water | 44.88% by weight |

EXAMPLE 2

| | |
|---|---|
| sodium alginate | 1.00% by weight |
| p-hydroxybenzoic acid methyl ester, sodium salt | 0.10% by weight |
| glycerin | 25.00% by weight |
| potassium monofluorophosphate | 0.75% by weight |
| aroma | 1.00% by weight |
| bromochlorophenol | 0.05% by weight |
| saccharin sodium | 0.06% by weight |
| pigment | 0.02% by weight |
| dicalciumphosphate dihydrate | 45.00% by weight |
| dicalciumphosphate, anhydrous | 8.00% by weight |
| sodium aluminum silicate (zeolite A, $Na_{12}(AlO_2)_{12}(SiO_2)_{12} \cdot 27H_2O$) | 0.50% by weight |
| sodium lauryl sulfate | 1.60% by weight |
| water | 17.92% by weight |

EXAMPLE 3

| | |
|---|---|
| carboxymethyl cellulose | 1.00% by weight |
| formalin | 0.50% by weight |
| p-hydroxybenzoic acid methyl ester | 0.07% by weight |
| 1,2-propylene glycol | 3.00% by weight |

-continued

| | |
|---|---|
| glycerine | 17.00% by weight |
| aroma | 1.20% by weight |
| dicalcium phosphate | 40.00% by weight |
| sodium aluminum silicate ($Na_2O \cdot Al_2O_3 \cdot 2SiO_2 \cdot 4,5H_2O$) | 2.00% by weight |
| saccharinate sodium | 0.12% by weight |
| sodium cyclamate | 0.02% by weight |
| sodium monofluorophosphate | 0.75% by weight |
| herbal extract | 1.50% by weight |
| pigment | 0.01% by weight |
| sodium lauryl sulfate | 2.00% by weight |
| water | 31.28% by weight |

EXAMPLE 4

| | |
|---|---|
| carboxymethyl cellulose | 1.10% by weight |
| benzoic acid | 0.20% by weight |
| p-hydroxybenzoic acid propyl ester | 0.05% by weight |
| glycerine | 20.00% by weight |
| 1,2-propylene glycol | 4.00% by weight |
| tetracalcium pyrophosphate | 45.00% by weight |
| sodium aluminum silicate (zeolite A, $Na_{12}(AlO_2)_{12}(SiO_2)_{12} \cdot 27H_2O$) | 4.00% by weight |
| sodium monofluorophosphate | 0.75% by weight |
| sodium lauroyl sarcosinate | 1.80% by weight |
| aroma | 1.00% by weight |
| saccharin sodium | 0.09% by weight |
| water | 22.01% by weight |

The sodium aluminum silicate in the examplary compositions may be entirely or partially replaced by the corresponding respective lithium or potassium compound. The particle size distribution of the zeolite used is such that at least 97% is less than 15 μm, at least 95% is less than 10 μm and about 40% is less than 5 μm.

We claim:

1. A non-corrosive aqueous-based toothpaste composition comprising about 0.05% to about 5% by weight of an anticorrosive additive which inhibits toothpaste corrosion of aluminum, said additive being a synthetic alkali metal aluminum silicate zeolite of the formula $$x(M.AlO_2).ySiO_2.zH_2O$$

wherein M is alkali metal or ammonium, X is a number from 1 to 64, y is a number dependent on X with the determination of y being one-fold to six-fold of X, and Z is a number from 0 to 256.

2. The non-corrosive toothpaste of claim 1 wherein M is sodium.

3. The non-corrosive toothpaste of claim 2 wherein the additive is a zeolite of the empirical formula $$Na_{12}(AlO_2)_{12}.(SiO_2)_{12}.27H_2O.$$

4. The non-corrosive toothpaste of claim 1 wherein the zeolite has a particle size distribution wherein at least 97% of the particles are smaller than 15 μm and about 40% are smaller than 5 μm.

* * * * *